(12) United States Patent
Glacer

(10) Patent No.: US 10,347,814 B2
(45) Date of Patent: Jul. 9, 2019

(54) MEMS HEATER OR EMITTER STRUCTURE FOR FAST HEATING AND COOLING CYCLES

(71) Applicant: Infineon Technologies AG, Neubiberg (DE)

(72) Inventor: Christoph Glacer, Munich (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 346 days.

(21) Appl. No.: 15/089,027

(22) Filed: Apr. 1, 2016

(65) Prior Publication Data

US 2017/0288125 A1    Oct. 5, 2017

(51) Int. Cl.
*H01L 41/08* (2006.01)
*H02N 1/00* (2006.01)
(Continued)

(52) U.S. Cl.
CPC ........ *H01L 41/0805* (2013.01); *B81B 7/0087* (2013.01); *H02N 1/006* (2013.01); *H05B 1/0288* (2013.01); *B81B 2201/018* (2013.01)

(58) Field of Classification Search
CPC ... H01L 41/0805; H01L 41/09; H01L 41/081; H01L 41/083; H01L 2924/00; H01L 2924/15; H01L 2924/15151; H01L 2924/15153; H01L 2924/1616; H01L 2924/1617; H01L 2924/1619; H01L 2924/3512; B81B 7/0087; B81B 2201/018; H02N 1/006; H05B 1/0288; H05B 1/023; H05B 1/0233; H05B 3/0014; B81C 1/00158; B81C 1/00166; B81C 1/00182; B81C 1/0019; B81C 1/00198; B81C 2203/0721; B81C 2203/0714; B81C 2203/0764; B81C 2203/0771

See application file for complete search history.

(56) References Cited

U.S. PATENT DOCUMENTS

| 6,376,787 | B1 | 4/2002 | Martin et al. |
| 6,452,124 | B1 | 9/2002 | York et al. |

(Continued)

FOREIGN PATENT DOCUMENTS

| CN | 101919079 A | 12/2010 |
| CN | 102197293 A | 9/2011 |

(Continued)

OTHER PUBLICATIONS

Schell, et al., "Demand Control Ventilation Using CO2", Ashrae Journal, New York 43.2, ashraejournal.org, Feb. 2001, 6 pages.

(Continued)

*Primary Examiner* — Shawntina T Fuqua
(74) *Attorney, Agent, or Firm* — Slater Matsil, LLP

(57) ABSTRACT

According to various embodiments, a MEMS device includes a substrate, an electrically movable heating element having a first node coupled to a first terminal of a first voltage source and the second node coupled to a reference voltage source, a first anchor anchoring the first node and a second anchor anchoring the second node of the electrically movable heating element to the substrate, and a cavity between the first anchor and the second anchor and between the electrically movable heating element and the substrate.

17 Claims, 17 Drawing Sheets

(51) Int. Cl.
*H05B 1/02* (2006.01)
*B81B 7/00* (2006.01)

(56) References Cited

U.S. PATENT DOCUMENTS

| | | | |
|---|---|---|---|
| 6,633,693 | B1 | 10/2003 | Peale et al. |
| 6,750,596 | B2 | 6/2004 | Kim et al. |
| 6,777,765 | B2 | 8/2004 | Chen et al. |
| 9,417,186 | B2 | 8/2016 | Jakoby et al. |
| 2003/0080839 | A1 | 5/2003 | Wong |
| 2004/0119126 | A1 | 6/2004 | Chen et al. |
| 2009/0040008 | A1* | 2/2009 | Aksyuk ............ B81B 3/0024 337/333 |
| 2010/0126834 | A1* | 5/2010 | Ikehashi ............ G11C 23/00 200/181 |
| 2010/0277040 | A1 | 11/2010 | Klee et al. |
| 2012/0118060 | A1 | 5/2012 | Kimura |
| 2012/0297860 | A1 | 11/2012 | Izawa et al. |
| 2013/0313675 | A1 | 11/2013 | Nakano et al. |
| 2015/0101395 | A1 | 4/2015 | Dehe et al. |
| 2015/0102372 | A1 | 4/2015 | Dehe et al. |

FOREIGN PATENT DOCUMENTS

| | | |
|---|---|---|
| CN | 103380353 A | 10/2013 |
| CN | 104817054 A | 8/2015 |
| DE | 102004030380 A1 | 1/2006 |
| DE | 102006059091 A1 | 7/2007 |
| DE | 102013206755 A1 | 10/2013 |
| EP | 1640771 A1 | 3/2006 |
| FR | 2766962 A1 | 2/1999 |
| GB | 2501681 A | 11/2013 |
| WO | 2013159075 A1 | 10/2013 |

OTHER PUBLICATIONS

Zosel, et al., "The measurement of dissolved and gaseous carbon dioxide concentration", Topical Review, IOP Publishing, LTD, Measurement Science and Technology, vol. 22, No. 7, May 2011, 47 pages.
Sauer, M., U. Schiller, and M. Arndt. "A Climate Control Sensor for optimizing the circulating-air mode by controlling the CO2 level inside the passenger compartment." 1st European Mobile Air Conditioning Workshop. 2005, 7 pages.
Hodgkinson, et al., "Non-dispersive infra-red (NDIR) measurement of carbon dioxide at 4.24.2μm in a compact and optically efficient sensor.", Sensors and Actuators B: Chemical, vol. 186, Sep. 2013, 21 Pages.
De Souza, Michelly, et al. "Thin-film lateral SOI PIN diodes for thermal sensing reaching the cryogenic regime." Journal Integrated Circuits and Systems 5.2 (2010): 8 pages.
Liu, et al., "A Micromachined Flow Shear Stress Sensor based on Thermal Transfer Principles", Journal of Microelectromechanical Systems, vol. 8, Issue: 1, Mar. 1999, 24 pages.
Ma, et al., "Methane Detection with High Temperature All-silicon Microheater", Sensors, 2014 IEEE, Dec. 2014—ieeexplore.ieee. org, 4 pages.
Mastrangelo, et al., "V Acuum-Sealed Silicon Micromachined Incandescent Light Source", Electron Devices Meeting, 1989, IEDM '89. Technical Digest., International—ieeexplore.ieee.org, 4 pages.

\* cited by examiner

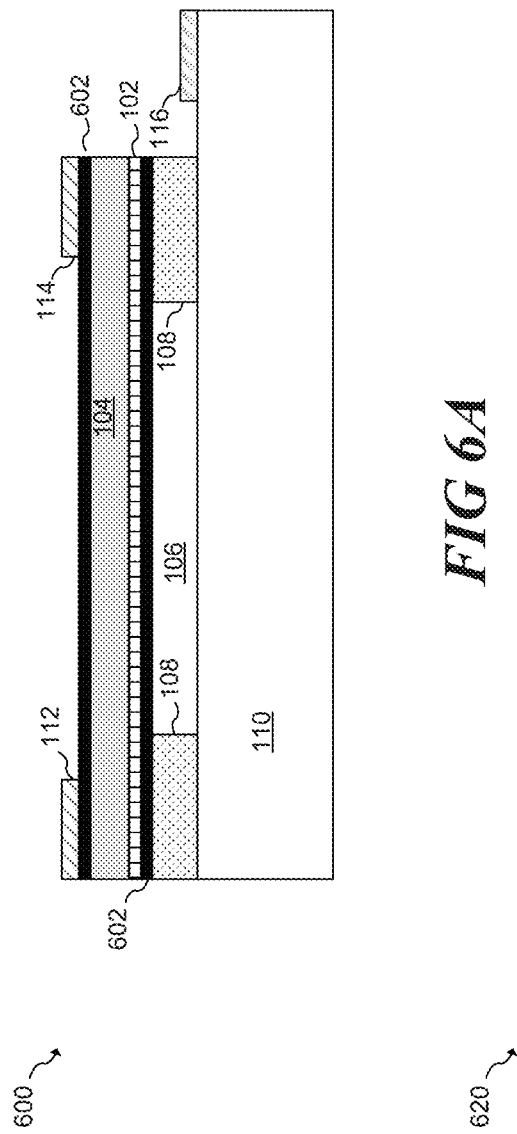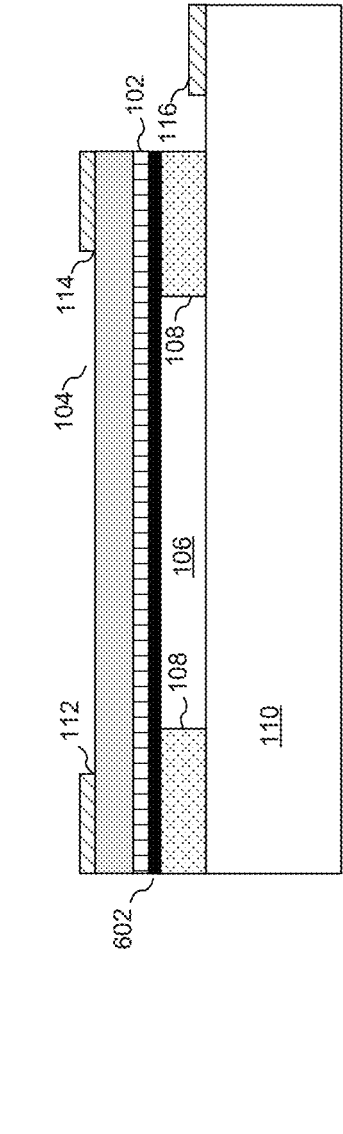
FIG. 6A
FIG. 6B

MEMS HEATER OR EMITTER STRUCTURE FOR FAST HEATING AND COOLING CYCLES

TECHNICAL FIELD

The present invention relates generally to a system and method of a MEMS device, and, in particular embodiments, to a system and method for controlling fast heating and cooling of a MEMS structure.

BACKGROUND

Micro-Electro-Mechanical Systems (MEMS), which in general include miniaturizations of various electrical and mechanical components, are produced by a variety of materials and manufacturing methods, and are useful in a wide variety of applications. These applications include automotive electronics, medical equipment, and smart portable electronics such as cell phones, Personal Digital Assistants, (PDA) hard disk drives, computer peripherals, and wireless devices. In these applications, MEMS may be used as sensors, actuators, accelerometers, switches, micro-mirrors and many other devices.

MEMS are used for use in temperature sensors to measure temperature or applications where they need to be heated and emit infra-red light. In such applications, MEMS structure may need to respond quickly and accurately to a heating signal. In some applications, the signal may require a quick cooling after a heating cycle. Various attributes that may be taken into design consideration include, for example, thermal response, geometry and temperature sensitivity. Joule heating is often used in MEMS structure where heat is produced as a result of current flowing through the structure. Energy is dissipated across the resistance of the structure that results in heat dissipation. In a MEMS structure, a heating element is often suspended in a cavity to achieve thermal isolation. The heating element may also exhibit actuation and emit infra-red light based on the current flow through the heating element.

SUMMARY

According to various embodiments, a MEMS device includes a substrate, an electrically movable heating element having a first node coupled to a first terminal of a first voltage source and the second node coupled to a reference voltage source, a first anchor anchoring the first node and a second anchor anchoring the second node of the electrically movable heating element to the substrate, and a cavity between the first anchor and the second anchor and between the electrically movable heating element and the substrate.

BRIEF DESCRIPTION OF THE DRAWINGS

For a more complete understanding of the present invention, and the advantages thereof, reference is now made to the following descriptions taken in conjunction with the accompanying drawings, in which:

FIG. 6A illustrates a cross-sectional view of another embodiment MEMS heating device with the heating element and membrane encapsulated by a tensile layer;

FIG. 6B illustrates a cross-sectional view of another embodiment MEMS heating device with the heating element having a tensile layer at the bottom and above the cavity;

FIG. 13, illustrate examples of implementation of embodiments of the present invention;

DETAILED DESCRIPTION OF ILLUSTRATIVE EMBODIMENTS

Figure 1A:
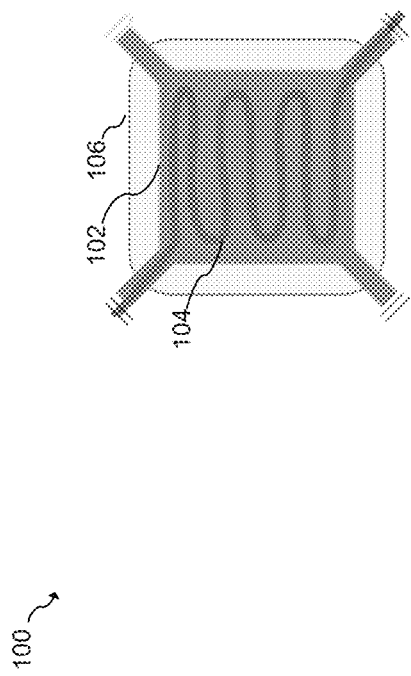
FIG. 1A illustrates a top view of a conventional micro electro-mechanical system (MEMS) heating device.

The making and using of various embodiments are discussed in detail below. It should be appreciated, however, that the various embodiments described herein are applicable in a wide variety of specific contexts. The specific embodiments discussed are merely illustrative of specific ways to make and use various embodiments, and should not be construed in a limited scope.

The present invention will be described with respect to preferred embodiments in a specific context, namely a system and method for controlling a fast heating and cooling of a micro-electrical mechanical system (MEMS) device. Some of the various embodiments described herein include MEMS heating elements, MEMS substrate, cavities in MEMS substrate and interface circuit. Other embodiments of the present invention may also be applied to various systems that utilize heating or cooling by a MEMS device, for example, temperature sensors, infra-red light emitters, thermal flow sensors, photo-acoustic devices, micro-actuators and many other devices or applications.

As the miniaturization of semi-conductor devices continues, MEMS devices are getting increasingly popular and finding a wide variety of applications in devices, such as heaters, temperature sensors, micro-actuators, photo-acoustic devices, micro-hotplate gas sensors, and the like. These applications include one or more MEMS heating elements designed to achieve optimum heating and cooling in a controlled manner. The heating can be achieved in different ways, including Joule heating. In some applications, a heating efficiency may be increased by having the MEMS heating element placed on a thermally isolated micro-machined platform called a membrane, in some cases a carrier plate.

Joule heating is related to a coupling between an electrical and a thermal phenomenon in a semiconductor device. Furthermore, Joule heating in a MEMS device combines electro-thermo-mechanical (ETM) effects, whereby the structure can be actuated based on an electrical potential across the device. A conductive layer in a MEMS structure can be heated quickly by applying an electric potential across the structure and allowing a current flow through the conductive layer. The current flow dissipates power across the resistance of the conductive layer and the temperature of the conductive layer is increased. In order to retain the heat energy by Joule heating, the MEMS structure generally includes a conductor layer on a membrane or a carrier plate suspended inside an open cavity. The cavity acts as a thermal insulator. The conductor layer may consist of small mass so that the heating can be fast. The cavity provides a large thermal resistance or insulation to the substrate, thereby allowing good thermal efficiency during heating.

A large thermal resistance between the heating element and the substrate during cooling results in slow dissipation of heat and renders the cooling process inefficient. The presence of a cavity aids in rapid heating but obstructs in rapid cooling. MEMS heating element suspended in a cavity above a substrate during a cooling period may not efficiently dissipate heat for a rapid cooling.

Figure 1B:
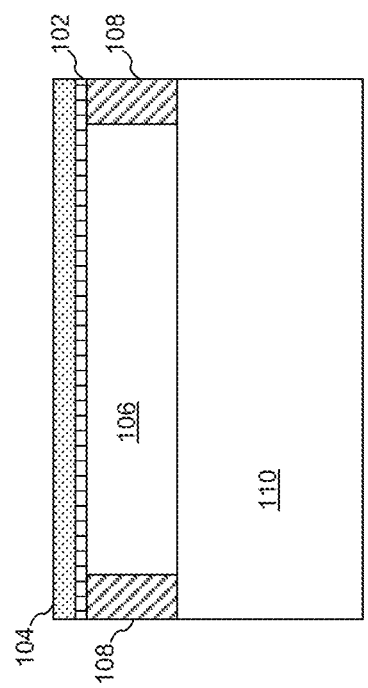
FIG. 1B illustrates a cross-sectional view of the MEMS heating device.

FIG. 1A illustrates a top view of a MEMS structure 100 that includes a heating element 104 of a resistive conductor layer and a membrane 102 inside a cavity 106. FIG. 1B shows schematic a cross-section of a MEMS structure 100, which, to simplify the discussion, does not necessarily correspond to any true cross-section of the device (and does not correspond to any cross-section of the plan view of FIG. 1A).

The cavity 106 thermally isolates the heating element 104 from a substrate. A current flow across the heating element 104 gives rise to the temperature of heating element 104. A smaller mass of heating element 104 provides faster rise in the temperature of heating element 104 during a heating cycle. The air in cavity 106 acts as a thermal isolator and allows the heat to be retained by heating element 104. The presence of a cavity 106 underneath heating element 104 and membrane 102 provides large thermal impedance between heating element 104 and the substrate. Large thermal impedance thereby allows a rapid heating and an increase in thermal efficiency.

As shown in FIG. 1B, membrane 102 and heating element 104 are suspended over cavity 106. Heating element 104 and membrane 102 are supported above a substrate 110 with by anchor 108. Anchor 108 can be formed as one continuous structure surrounding the cavity 106 over substrate 110. Cavity 106 is located underneath membrane 102 and above substrate 110. Based on the application, cavity 106 may be filled with air or any gaseous element or a vacuum. Anchor 108 is made of dielectric material and acts as thermal isolator for membrane 102 and heating element 104 from substrate 110.

The MEMS substrate 110 can be formed of materials, for example, silicon, germanium, and gallium arsenide. According to various embodiments, MEMS substrate 110 may be doped with p-type or n-type impurities. In another embodiment, substrate may be formed of a metal for efficient heat transfer.

Anchor 108 is formed of dielectric material that may include silicon dioxide, silicon carbide, silicon nitride, and so forth. An insulating layer 118 is built underneath heating element 104 and above anchor 108. Insulating layer 118 is supported by anchor 108 above MEMS substrate 110 and a cavity 106. In other embodiments, insulating layer 118 may be formed of a high-strength electric insulator silicon nitride, for example.

The heating element 104 is implemented by a resistive conductor material that may be formed in various ways. In various embodiments, heating element 104 may be formed of metals such as platinum and tungsten. In other embodiments, non-metals such as poly-silicon, silicon carbide, amorphous or single crystal silicon, and the like can be used. A heat spreader can be implemented in the same layer as the heating electrode 104 to more effectively and evenly spread heat across membrane 102. The heat spreader would generally not be electrically connected to the heating element.

In some applications, MEMS structure 100 can be used as a temperature sensor for a gaseous media, where cavity 106 is filled with the gaseous media. The gaseous media prevents rapid heat dissipation by heating element 104 due to its poor thermal conduction. When heating element 104 is used as a temperature sensor this poor thermal conduction may lead to inaccuracies in the temperature measurements. In an embodiment, an array of heating element may be formed in a single substrate to heat a device. In another embodiment, the device to be heated may be placed above the array of the heating element.

Thermal management is a consideration in designing MEMS devices. The generation of heat via a MEMS device often involves a Joule heating where a voltage is applied to a MEMS heating element of the MEMS device and heat is generated due to the flow of an electrical current through the MEMS heating element. The Joule heating is defined by Joule's law, the equation is given by:

$$Q = j^2 \rho \qquad (1)$$

where j is a current density vector having a unit Amp/m2, $\rho$ is a specific electric resistivity expressed as ohms-m, and Q is a generated heat per unit volume defined by a unit Watt/m3. The specific electric resistivity $\rho$ is a function of the type, the shape and the structure of the material used as the MEMS heating element.

The voltage used for the Joule heating can be pulsed at a specific period based on an application. The heating is done when a voltage is applied across a conductive layer of a heating element and causes a current flow. When applying a pulsed voltage to heat a conductive layer of the heating element, the heating follows thermal profile that is a function of a time constant. The time constant is a function of a thermal resistance of the heating element to the substrate or the heat sink. A fast heating can be achieved with a large thermal resistance and with a fast slew rate of current that is flowing through the heating element. Alternatively, a fast cooling can be achieved by a small thermal resistance to the substrate or the heat sink and a fast slew rate of the current.

In an embodiment of the present invention, a MEMS structure is designed to allow a fast heating by applying a voltage across a MEMS heating element and allowing a fast cooling by actuating the MEMS heating element to make a contact with a MEMS substrate. An actuation of the MEMS heating element to establish a contact with the MEMS substrate is done by generating an electrostatic force between the heating element and the MEMS substrate. Having a surface contact with the MEMS substrate, the MEMS heating element achieves very low thermal impedance to the substrate of the MEMS structure.

Actuation of the MEMS heating element can be described with an electrostatic force that attracts two oppositely charged elements at a specific distance. The electrostatic force F is given by the Coulomb's equation:

$$F = \frac{Q1 * Q2}{d^2} \quad (2)$$

where k is constant, Q1, Q2 are electric charges and d is the distance between the two charged elements. In an embodiment of the present invention, a MEMS heater element is charged to a high potential and the MEMS substrate is charged to a ground potential in order to create the electrostatic force F between them. According to various embodiments, different actuation methods and elements, for example, piezo sensors, thermal expansion can be used to actuate the heating element to make a contact with a MEMS substrate.

Figure 2A:
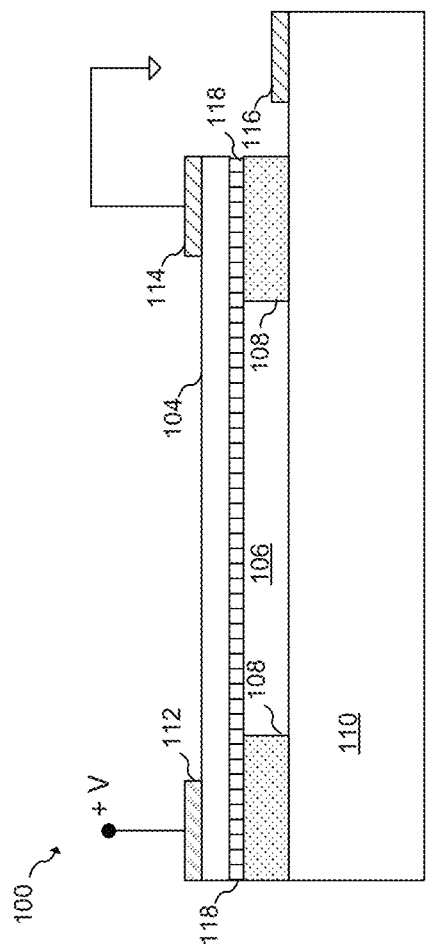
FIG. 2A illustrates a cross-sectional view of an embodiment MEMS heating device during a heating cycle.
Figure 2B:
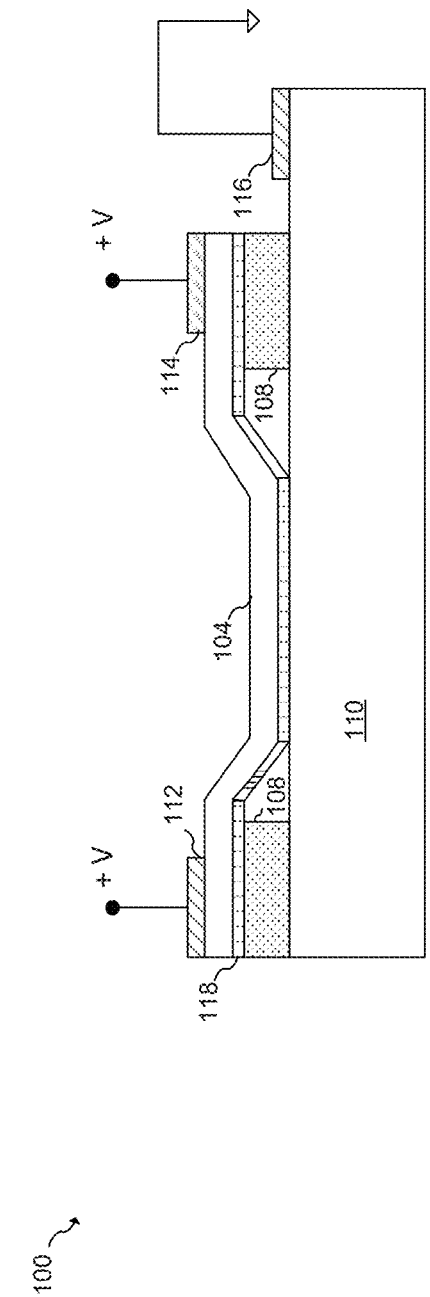
FIG. 2B illustrates a cross-sectional view of an embodiment MEMS heating device during a cooling cycle.

FIG. 2A illustrates a cross-sectional view of an embodiment MEMS heater 100 during a heating cycle, while FIG. 2B illustrates a cross-sectional view of the same embodiment MEMS heater 100 during a cooling cycle.

FIGS. 2A and 2B are similar to FIG. 1B but includes additional details to illustrate the device in operation. For example, electrical contacts 112 and 114 are made to heating element 104 at two opposite ends. In some embodiments, electrical contacts 112 and 114 may be formed by aluminum, titanium nitride, tungsten etc.

Electrical contact 112 is used for a connection to a high potential of a voltage source and electrical contact 114 is connected to a ground reference during a heating cycle. Another electrical contact 116 is made to MEMS substrate 110 that remains open during the heating cycle. During the heating cycle, electrical current flows due to a potential difference between electrical contacts 112 and 114 via heating element 104 and causes a Joule heating. Insulating layer 118 prevents any electrical current flow between the heating element 104 and MEMS substrate 110 when they are in contact with each other. In this configuration, heating element 104 remains separated, e.g., thermally insulated, from MEMS substrate 110 by the cavity 106.

FIG. 2B illustrates a cross-sectional view of the embodiment MEMS heater 100 during a cooling cycle. In this configuration, a voltage potential is created between the heating element 104 and the substrate 110 to cause the heating element 104 and insulating layer 118 to make contact with MEMS substrate 110 inside the cavity 106.

In switching from the heating cycle, the reference supply connection to the heating element 104 is removed from electrical contact 114 and electrical contact 116 is connected to the ground reference. The electrical contact 114 can be set to the voltage +V as illustrated or allowed to float. In another configuration, electrical contact 116 is allowed to float while the voltage +V is connected to electrical contact 114. In other embodiments, other voltages can be applied to achieve the same results.

In the example of FIGS. 2A and 2B, an insulating layer 118 prevents heating element 104 from making a direct contact with MEMS substrate 110, e.g., to prevent current flow into the substrate and the heating element 104 from sticking to the substrate 110. In this example, the movable portion includes heating element 104 and insulating layer 118 but not the membrane layer 102 in FIG. 1B. It is understood that the insulating layer 118 may be the membrane layer or the structure can include separate layers. In fact, in certain embodiments, neither layer is needed and the heating element 104 is the only portion deflected during operation.

Returning to the operation illustrated in FIG. 2B, a portion of heating element 104 and insulating layer 118, which are suspended inside the cavity 106 during heating cycle, are deflected and pulled down to make contact with MEMS substrate 110. The deflection occurs at both ends of the heating element 104 and insulating layer 118. Anchor 108 prevents the ends of the heating element 104 and insulating layer 118 from being deflected. The area of the heating element 104 and insulating layer 118 on top of the anchors 108 remains anchored at both ends. The anchor 108 is one continuous structure surrounding cavity 106.

Figure 3:
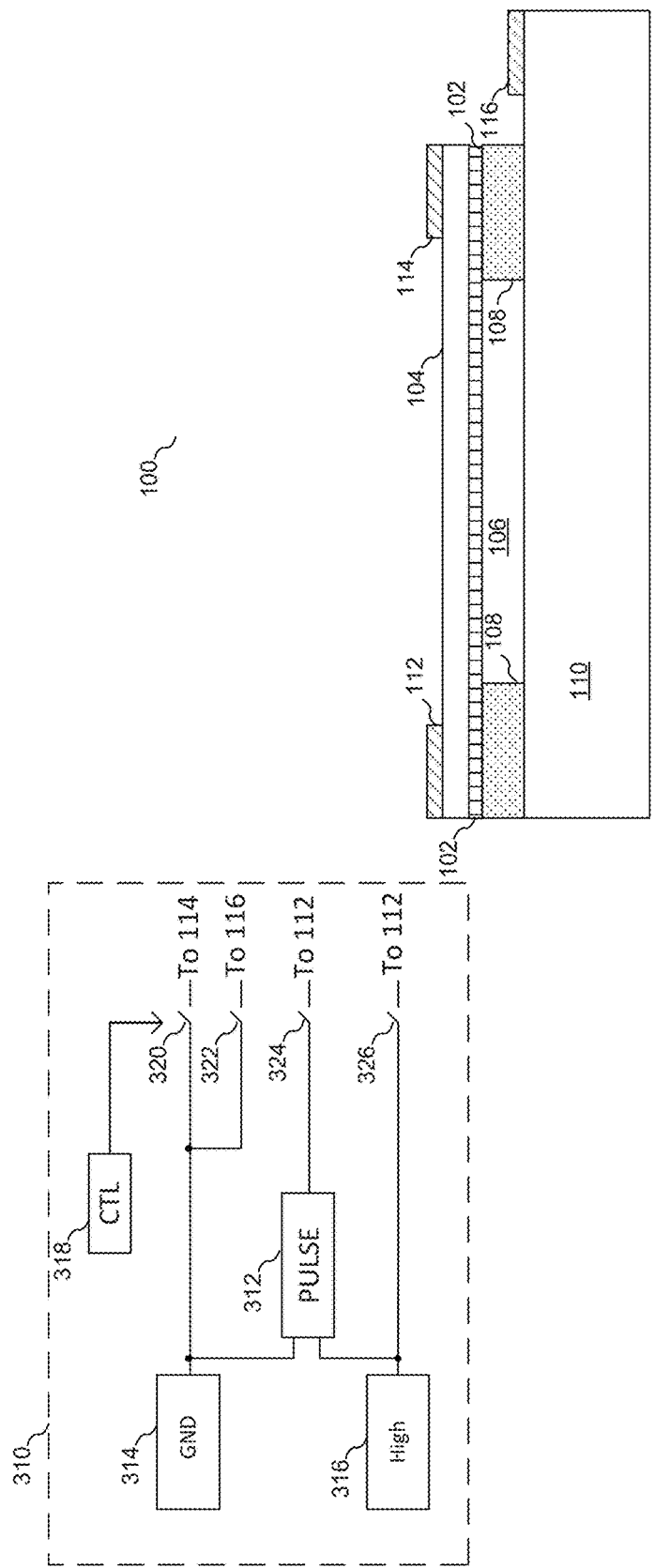
FIG. 3 illustrates another embodiment of MEMS heating device controlled by a control circuit.

FIG. 3 illustrates a cross-section of an embodiment MEMS heater 100 with a control circuit 310 controlling a heating and cooling of heating element 104. Control circuit 310 sends electrical signals to heating element 104 and MEMS substrate 110 based on a heating and a cooling cycle. In this example, the MEMS device 100 receives a high reference from voltage source 316 (e.g., +V), a low reference from voltage source 314 (e.g., ground) and a pulsed voltage from pulse generator 312. These voltages are controlled by control circuitry 318, which controls switches 320-326.

The pulse generator 312 is controlled by switch 324 to be coupled to electrical contact 112 during the heating cycle. While not implemented in this particular circuit, the pulse generator 312 can be coupled to electrical contact 112 and/or electrical contacts 114 during a cooling cycle. The period is designed based on the application. In an embodiment, the frequency of the pulse generator is between 5 to 10 Hz. In other embodiments, the frequency can be lower or higher. For example, the frequency could be in the hundreds of Hertz.

In the illustrated example, the ground reference voltage 314 is controlled by control switch 320 to be coupled to electrical contact 114 during a heating cycle and is controlled by switch 322 to be coupled to electrical contact 116 during a cooling cycle. Likewise, the high reference voltage 316 is controlled by switch 326 to be coupled to electrical contact 112 during a heating cycle and a cooling cycle.

It should be noted that while one configuration of control circuit 310 is illustrated, those skilled in the art may recognize that control circuit 310 can be implemented in various different ways. In an embodiment, control circuit 310 can be formed in the same MEMS substrate. In another embodiment, control circuit 310 can be a part of another integrated circuit (IC). In various embodiments, an array of heating elements 104 may be controlled by a single control circuit 310. In another embodiment, each heating element may have their own control circuit 310 to allow an independent control of heating element 104 during a heating and a cooling operation.

Figure 4A:
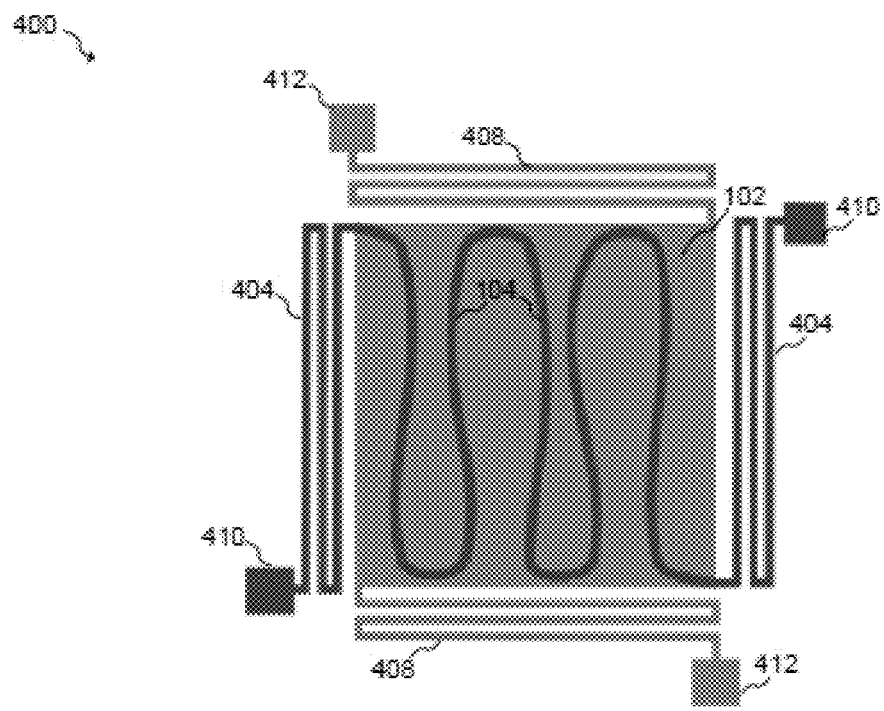
FIG. 4A illustrates a top view of a MEMS heating device with spring supports for a heating element and a membrane at opposite ends.
Figure 4B:
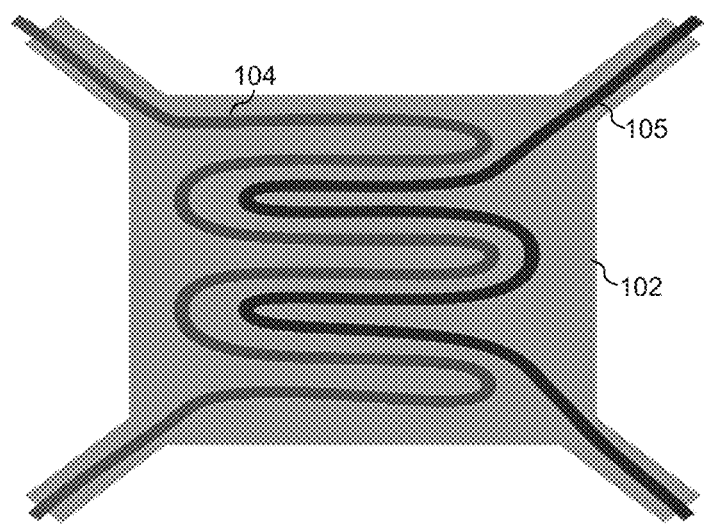
FIG. 4B illustrates a top view of a MEMS heating device that includes a sensing electrode.

FIGS. 4A and 4B illustrate other embodiments. Referring to FIG. 4A, a MEMS heater 400 includes a heating element 104 having spring supports 404 at opposite ends of the MEMS structure. Each spring support 404 has a spring anchor 410 that is located on top of anchor 108. MEMS heater 400 also includes a membrane 102 formed under the heating element 104 that carries and provides support to heating element 104 while suspended in a cavity above a MEMS substrate. Spring supports 404 are electrically connected to heating element 104 and spring supports 408 are electrically connected to membrane 102 at two opposite ends. Each spring support 408 includes a spring anchor 412 that is placed on top of anchor 108 above MEMS substrate 110 to suspend heating element 104 and membrane 102 above the MEMS substrate and inside the cavity.

Membrane 102 is formed in a rectangular shape and heating element 104 is formed in a serpentine shape to allow smaller heating mass. A smaller mass provides a faster heating with smaller voltage across the heating element. However, in another embodiment, the heating element 104 can be formed in a rectangular shape or any other shape supported by membrane 102. Spring supports at both ends of membrane 102 and heating element 104 allow reduced actuation voltage and larger surface contact to the substrate during heat transfer in a cooling cycle.

FIG. 4B illustrates an embodiment that includes a second serpentine structure 105. This second structure 105 can be an electrode that is used for temperature sensing. As illustrated, the sensing structure 105 can be electrically connected to control circuitry (e.g., control circuit 310 of FIG. 3) using the two other anchors. Results of the sensing can be used to control the heating and cooling of the sensing heating element 104.

Other embodiments and variations are also envisioned. For example, force and sense electrodes can be used to eliminate parasitic contact resistances. It is understood that various ones of the embodiments and variations described herein can be used in combination.

Figure 5:
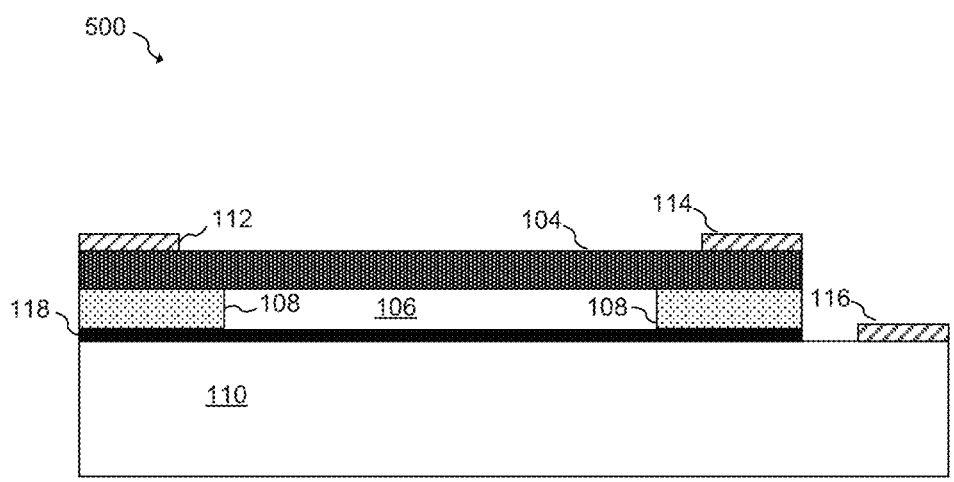
FIG. 5 illustrates a cross-sectional view of another embodiment MEMS heating device with an insulating layer that is formed above a substrate and below a cavity.

FIG. 5 illustrates a cross-section of an embodiment MEMS heater 500 that includes an electrical insulating layer 118 formed over MEMS substrate 110 instead of being attached to heating element 104 as shown in the embodiment of FIG. 2A. Forming electrical insulating layer 118 on MEMS substrate 110 rather than the membrane 102 eliminates mechanical influences that may have been exerted by electrical insulating layer 118 on membrane 102 during actuation in the previously described embodiment since electrical insulating layer 118 is not subjected to any actuation. The MEMS substrate 110 remains electrically isolated from the membrane 102 during cooling cycle. In another embodiment, an insulator 118 as previously described can be formed below the membrane 102, e.g., as shown in FIG. 2A.

FIGS. 6A and 6B illustrate another embodiment of MEMS heater 600 and 620 in which the heating element 104 is encapsulated by a coating of a tensile layer 602. Membrane 102 and heating element 104 can be coated on upper and or lower surfaces by a tensile layer 602. Tensile layer 602 provides flexibility of heating element 104 during actuation and facilitates contact of heating element 104 to MEMS substrate 110 during a cooling cycle. An electrical isolation from the substrate 110 by heating element 104 is also achieved by tensile layer 602 while in contact during the cooling cycle. FIG. 6A illustrates an example where the tensile layer 602 is formed on both top and bottom surfaces of the combination of membrane 102 and heating element 104 while FIG. 6B illustrates another embodiment of MEMS heater 620 that includes coating of a single tensile layer 602 at the bottom of the combination of membrane 102 and heating element 104. Coating can be made with different types of tensile layers. In an embodiment of the present invention, the tensile layer 602 may be formed with a layer of silicon nitride.

Figure 7:
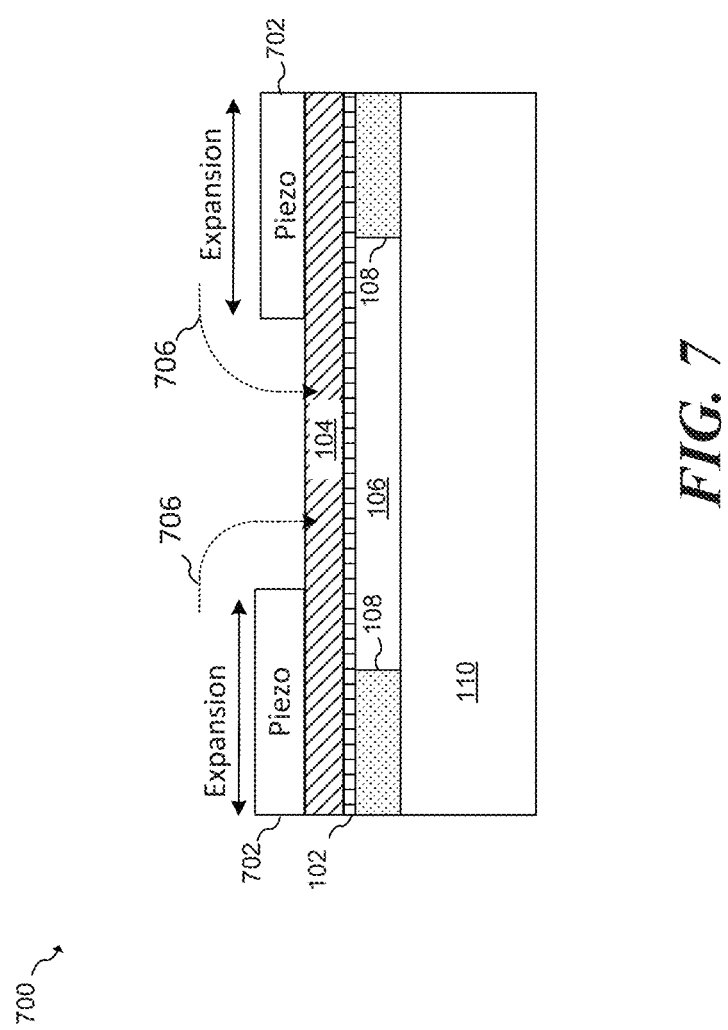
FIG. 7 illustrates a cross-sectional view of another embodiment MEMS heating device with Piezo elements above the heating element.

FIG. 7 illustrates another embodiment of MEMS heater 700 that includes a piezo device 702 formed at two ends of heating element 104. Piezo 702 at each end of heating element 104 clamps heating element 104 during an expansion. During expansion of piezos 702, downward bending moments, as illustrated by the arrows 706, are created on heating element 104 that cause heating element 104 to actuate downwards and make contact to MEMS substrate 110. Heating element 104 actuates upwards when piezos 702 at both ends contract. Thus, by expanding piezos 702, heating element 104 can be actuated downwards to make contact with MEMS substrate 110 to achieve rapid heat dissipation.

On the other hand, with a contraction of piezos 702, heating element 104 can be pulled away from MEMS substrate 110 to create a thermal isolation in cavity 106, to prevent heat energy loss during heating cycle. The membrane 102 is formed below heating element 104 to carry heating element 104. The actuation of heating element 104 causes membrane 102 to follow the actuation towards substrate 110. Alternatively, membrane 102 is actuated upwards and away from substrate 110 during contraction of piezos. In an embodiment of the present invention, a piezo may be formed by a thin film piezoelectric and structural materials above heating element 104.

Figure 8A:
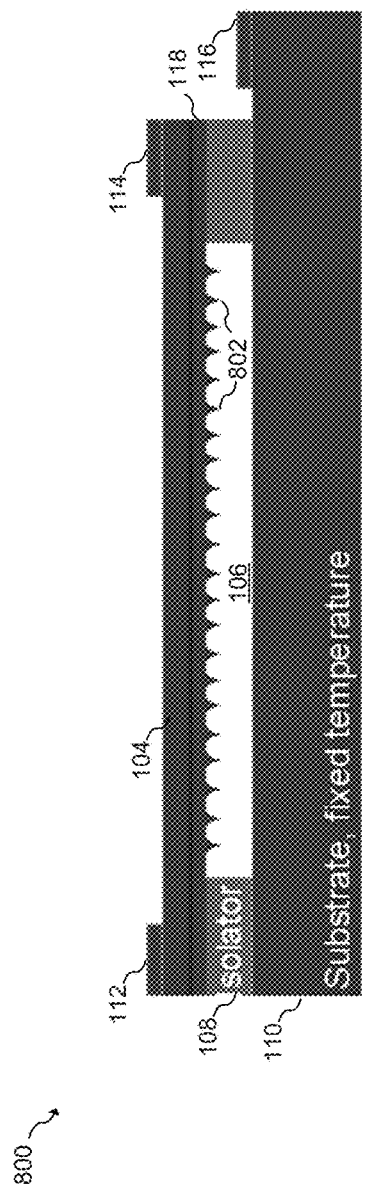
FIG. 8A illustrates a cross-sectional view of another embodiment MEMS heating device with stiction bumps formed in an insulation layer above the cavity.

FIG. 8A illustrates a cross-section view of an embodiment MEMS heater 800 that includes anti-stiction bumps 802 formed in an insulating layer 118. Anti-stiction bumps are small protrusions of isolation layer, e.g., with spiky tips, that prevent stiction of insulating layer 118 to MEMS substrate 110. A smooth surface of insulating layer 118 can remain attached to a smooth surface of MEMS substrate during the cooling cycle and may need additional force to be removed after the cooling cycle, be isolated from MEMS substrate. Anti-stiction bumps 802 with their spiky tips prevent stiction and allow insulating layer 118 and heating element 104 easy separation during operation.

Figure 8B:
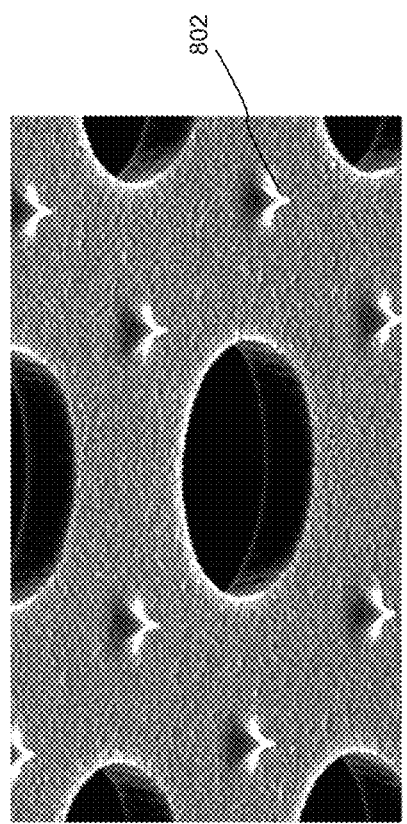
FIG. 8B illustrates an SEM image of stiction bumps shown in FIG. 8A.

FIG. 8B illustrates a scanning electron microscope (SEM) image of an insulating layer 118 with anti-stiction bumps 802. Anti-stiction bumps are created by using an additional mask that is used to create small squares or round holes etched in a sacrificial layer filling the cavity. Insulating layer 118 fills up these holes when insulating layer is deposited on top of the sacrificial layer. Once the resistive conductor layer forming heating element 104 is deposited, the sacrificial layer is removed; however, protruding structures in insulating layer filling up the squares or holes remain and create anti-stiction bumps 802 inside cavity 106. Tips of anti-stiction bumps can be made spiky by overexposing the sacrificial layer.

In another embodiment, stiction can be prevented by the heater itself. In particular, the heater temperature can prevent from stiction as the water responsible for sticion gets vaporized. This is another example of a mechanism to prevent stiction.

FIGS. 9A-9G illustrate an embodiment fabrication process flow for the embodiment MEMS device 100. As will be discussed below, simple surface micro mechanical processes with TEOS oxide and poly-crystalline silicon are used to form sacrificial layers as described above. Alternatives are possible, such as those explicitly mentioned and others that would be clear to one of ordinary skill.

Figure 9A:
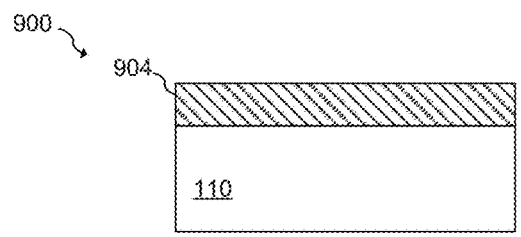
FIGS. 9A-9F illustrate a fabrication process flow for the embodiment MEMS heating device of FIG. 2A.

According to various embodiments, FIG. 9A begins with a wafer 900 that includes a substrate 110 and a dielectric layer 904 formed over substrate 110. In alternative embodiments, substrate 110 may be formed of silicon or other materials such as silicon germanium, silicon carbide, gallium arsenide, or the like. Substrate 110 may be a silicon-on-insulator (SOI) substrate. SOI substrate may include a layer of semiconductor material (e.g., silicon germanium, gallium arsenide, and the like) formed over an insulator layer (e.g., buried oxide), which is formed in a silicon substrate. Alternatively, other substrates that can be used include multi-layered substrates, gradient substrates, hybrid orientation substrates, and so forth.

Dielectric layer 904 is formed of a dielectric material, such as silicon dioxide (SiO2). Dielectric layer 904 formed by silicon dioxide acts as a strong thermal and electrical insulator. Dielectric layer 904 may be deposited over substrate 110 using, for example, spinning, chemical vapor disposition (CVD), plasma enhanced chemical vapor deposition (PECVD), low pressure CVD, or other suitable deposition techniques. In other embodiments, dielectric layer 904 may be formed of different suitable materials such as low-k dielectrics (e.g., carbon doped oxides), extremely low-k dielectrics (e.g., porous carbon doped silicon dioxide), a polymer (e.g., polyimide), combinations thereof, or the like. A portion of dielectric layer 904 may be removed in subsequent process steps in order to form an anchor or base for MEMS structures to substrate 110.

Figure 9B:
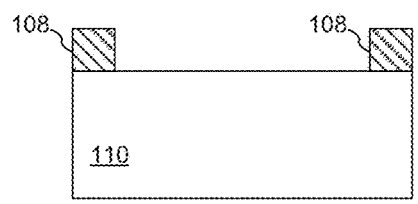

FIG. 9B illustrates a patterned dielectric layer 904 forming the anchor or a base 108 to support a MEMS structure above substrate 110. The patterning of dielectric layer 904 can be done using, for example, a combination of photolithography and etching techniques. Patterning of dielectric layer above substrate 110 may be performed by depositing a photoresist above dielectric layer 904. Liquid photoresist is placed on dielectric layer 904 across the wafer 900. Wafer 900 is spun at high speed to produce a thin and uniform coating of the photoresist. The photoresist is then exposed to selectively etch out a portion of dielectric layer 904 that forms a cavity above substrate 110. Different etching techniques may be used, for example, reactive ion etching (RIE), lateral etching, and the like, to remove the portion of dielectric layer 904.

Figure 9C:
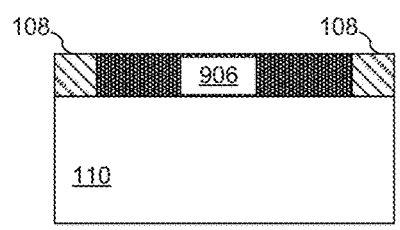

FIG. 9C illustrates the formation of a sacrificial layer 906 across wafer 900 that fills the cavity patterned and etched as described in the previous paragraph. Sacrificial layer 906 is chosen such that anchor 108 is not damaged during a removal of sacrificial layer 906 in the subsequent process. Various design requirements of MEMS structures are achieved by sacrificial layer 906 during the processing. Sacrificial layer 906 does not constitute any part of the final MEMS structure, and hence called a sacrificial layer. Suitable mechanical properties of sacrificial layer 906 may include, for example, good adhesion, low residual stresses to avoid delamination or cracking of the MEMS structure.

Figure 9D:
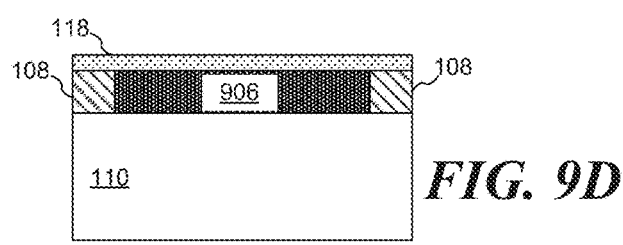

FIG. 9D illustrates a deposition of a sacrificial layer 906 above sacrificial layer 906. Sacrificial layer 906 may be formed by a silicon nitride (Si3N4) layer that has high-strength electric insulation property. Different types of deposition techniques used to deposit the silicon nitride over sacrificial layer 906 include, for example, a chemical vapor deposition (CVD), low pressure chemical vapor deposition (LPCVD), a plasma-enhanced chemical vapor deposition (PECVD), and others. In an embodiment, insulating layer is deposited with a thickness of 1400 Å.

Figure 9E:
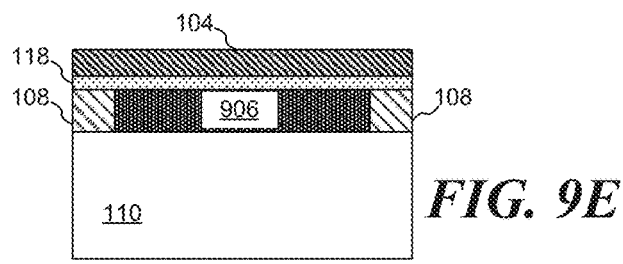

After deposition of sacrificial layer 906, a resistive conductor layer 104 is deposited as shown in FIG. 9E. Different types of material can be used for resistive conductor layer 104 that include, for example, poly silicon, silicon carbide, amorphous or single crystal silicon, and so forth. The deposition of resistive conductor layer 104 may be performed by a LPCVD or PECVD process. In an embodiment, resistive conductor layer 104 may be deposited with a thickness of 2800 Å. In an embodiment manufacturing process, resistive conductor layer 104 may go through a high temperature processing steps after deposition that may include, for example, doping, thermal oxidation, annealing, and so forth. Resistive conductor layer 104 may have different sheet resistance based on the application. A resistivity of resistive conductor layer 104 may be controlled by a phosphorous doping using, for example, an ion implantation process. However, other method, for example, diffusion may be used to control the resistivity of resistive conductor layer 104. In an embodiment, resistive conductor layer 104 has a sheet resistivity of 100 Ohm/square. In another embodiment, a thickness of the sacrificial layer 906 may be between 0.1 and 0.5 of a thickness of resistive conductor layer 104.

Figure 9F:
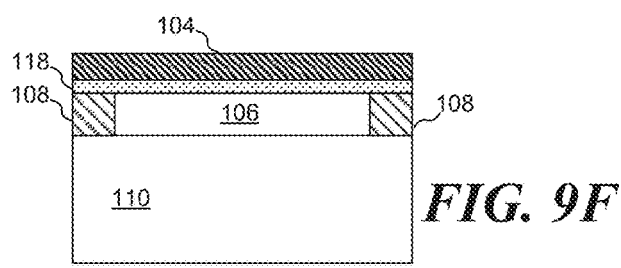

FIG. 9F illustrates a patterning process on resistive conductor layer 104. The patterning is performed, for example, using a combination of photolithography and etching. According to an embodiment, resistive conductor layer 104 is patterned in a rectangular shaped heating element. In an embodiment, patterning of resistive conductor layer 104 is done to create a serpentine heating element for a MEMS device. In another embodiment, patterning of resistive conductor layer is done to form a spring support at both ends of the serpentine heating element. Various shapes may be patterned for manufacturing the heating element based on the application.

Various modifications to the embodiment fabrication sequence described in FIGS. 9A-9F are envisioned. Further, the structure may be modified in numerous embodiments and modifications to the fabrication sequence will be expected. The various process steps described herein and the accompanying figures are illustrative. According to various embodiments, structures may include sloped sidewalls, rough surfaces, and numerous dimensions. Fabrication method may also be used as disclosed in U.S. patent application publication US 2015/0102372 A1 titled "Semiconductor Device for Emitting Frequency-Adjusted Infrared Light" filed Oct. 14, 2013, which is incorporated herein by reference in its entirety.

Figure 10A:
FIGS. 10A-10G illustrate a fabrication process flow for the embodiment MEMS heating device of FIG. 5.

FIGS. 10A-10G illustrate an embodiment manufacturing process flow for the embodiment MEMS device of FIG. 5. The process begins with substrate 110 of a wafer 1000 as shown in FIG. 10A. According to various embodiments, substrate 110 may be formed of silicon or other materials. In another embodiment, substrate 110 may be lightly doped with p-type material, for example.

Figure 10B:
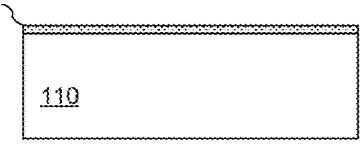

FIG. 10B illustrates a deposition of a thin insulating layer 118 above substrate 110. Thin insulating layer may be formed by a silicon nitride layer having a high-strength electrical insulation property. Various deposition techniques may be used to deposit insulating layer 118, for example, CVD, PECVD, LPCVD and other suitable deposition techniques. Thickness of thin insulating layer may vary based on different MEMS structures. In embodiments of the present invention, thin insulating layer 118 is deposited for a thickness of about 140 to 280 nm. These thicknesses can be larger or smaller in other applications.

Figure 10C:
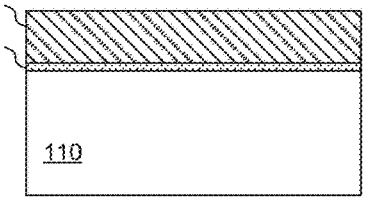
Figure 10D:
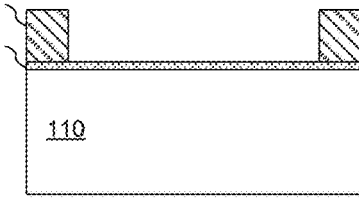

A dielectric layer 904 is formed by depositing a dielectric material, such as SiO$_2$ above thin insulating layer 118 as shown in FIG. 10C. The deposition may be done using various methods, for example, spinning CVD, PECVD, or other suitable deposition techniques. FIG. 10D illustrates a patterning of dielectric layer 904 to form the anchor or base 108 to support MEMS device above substrate 110 and sacrificial layer 906. The patterning of dielectric layer may be used to define a cavity 106 for the MEMS device shown in FIG. 5. The cavity is surrounded by anchor 108.

Figure 10E:
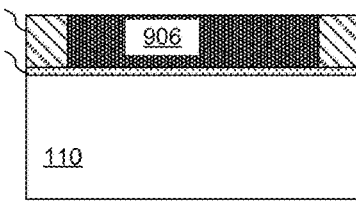
Figure 10F:
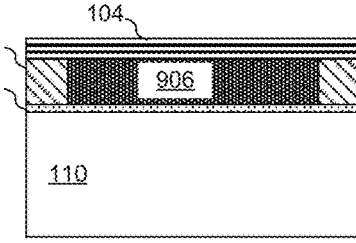

FIG. 10E illustrates deposition of a sacrificial layer 906 that fills up the cavity surrounded by anchor 108. Sacrificial layer 906 acts as a temporary mechanical layer onto which actual device layers, for example, poly-silicon for heating element, silicon nitride for membrane, and others can be deposited. FIG. 10F illustrates deposition of a resistive conductor layer 104 deposited above sacrificial layer 906. Resistive conductor layer 104 may be formed by different materials, for example, poly silicon, silicon carbide, and so forth.

Patterning of resistive conductor layer 104 may be performed with a combination of photolithography and etching process. A negative or a positive photoresist may be applied to resistive conductor layer 104 to pattern an embodiment MEMS heating element.

Figure 10G:
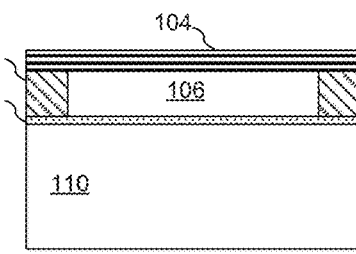

After patterning resistive conductor layer 104, sacrificial layer 906 is removed and cavity 106 is formed. The heating element remains suspended above the cavity and anchored at two ends as shown in FIG. 10G.

Figure 11A:
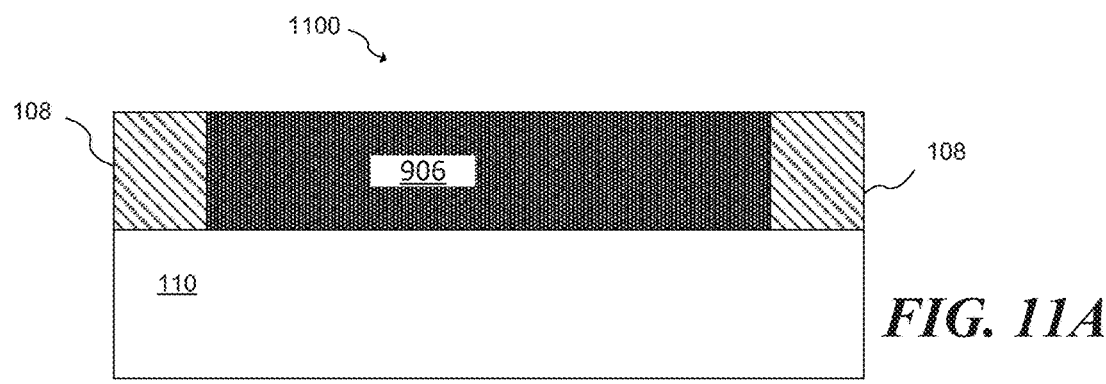
FIGS. 11A-11H illustrate a fabrication process flow for forming stiction bumps in MEMS heating device.
Figure 11B:
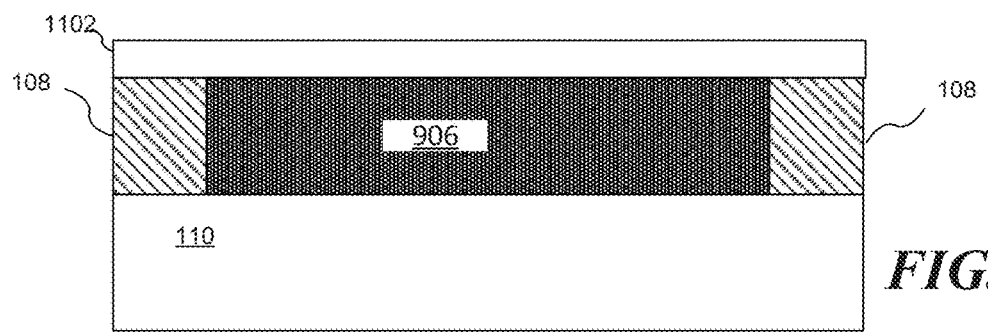
Figure 11C:
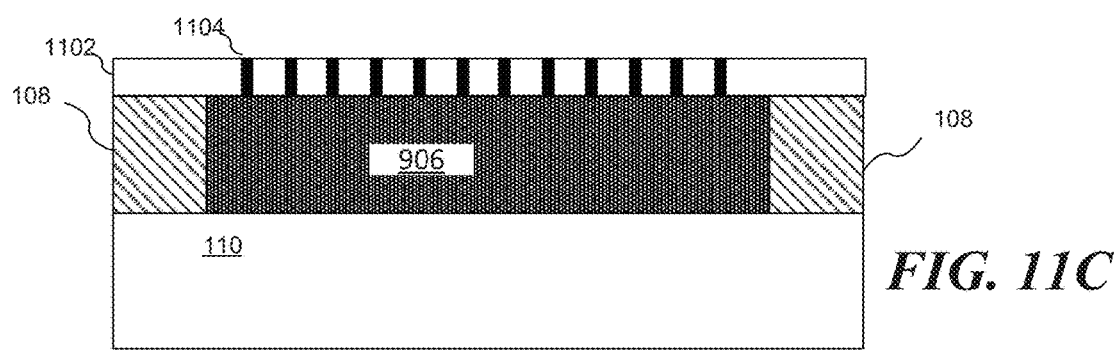

FIGS. 11A-11H illustrate an embodiment manufacturing process to form stiction bumps in insulating layer 118. FIG. 11A illustrates the step where sacrificial layer 906 is formed to cover a cavity inside anchor 108 and above substrate 110. A layer of photoresist 1102 is deposited over sacrificial layer 906 as illustrated in FIG. 11B. Photoresist 1102 is an organic polymer which changes its chemical structure when exposed to ultraviolet (UV) light. A deposition of photoresist 1102 may be done in various methods; one of these methods includes spin coating. Photoresist 1102 is then exposed with UV light to pattern stiction bump regions on sacrificial layer 906. FIG. 11C shows unexposed area 1104 of photoresist 1102. These unexposed area 1104 in photoresist 1102 are washed away to perform selective etching of sacrificial layer 906 to form stiction bumps.

Figure 11D:
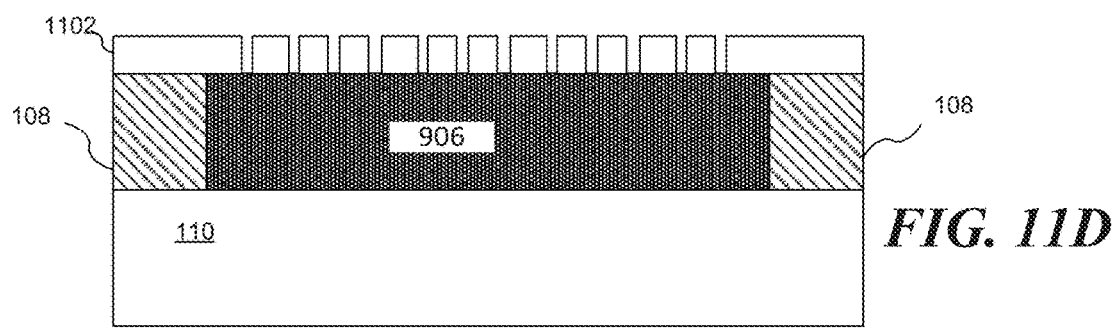
Figure 11E:
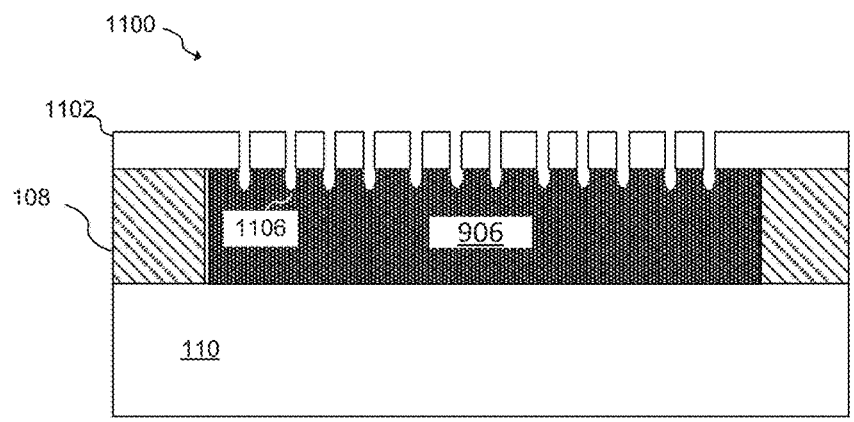
Figure 11F:
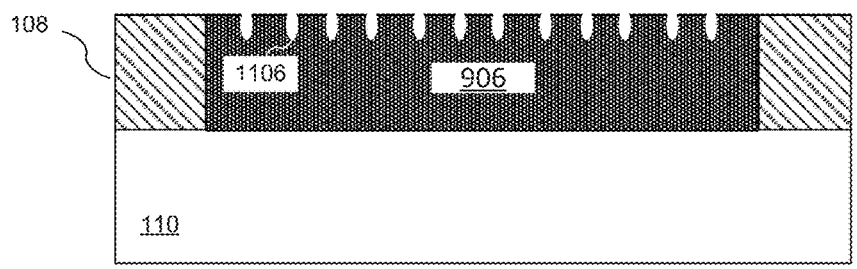

FIG. 11D shows such a process step where photoresist 1102 contains unexposed area 1104 to prepare for etching of sacrificial layer 906. FIG. 11E illustrates etching of sacrificial layer 906 to create stiction bumps 1106. Etching of sacrificial layer 906 may be done in various ways, an isotropic etching, anisotropic etching, wet or dry etching, plasma etching, for example. FIG. 11F illustrates the process step where photoresist 1102 is removed and sacrificial layer 906 contains grooves for stiction bumps 1106. Removal of photoresist may be done using various types of solvents.

Figure 11G:
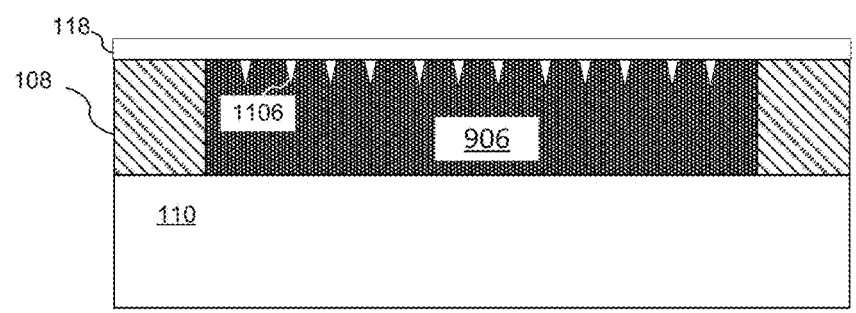
Figure 11H:
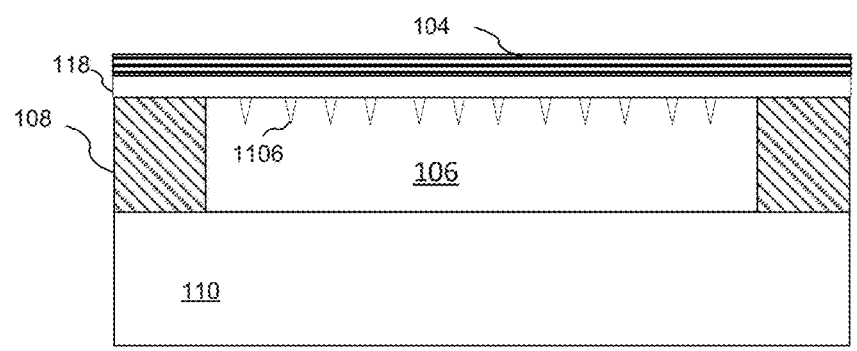

FIG. 11G illustrates the process step where sacrificial layer 906 is deposited over sacrificial layer 906 having the grooves for stiction bumps 1106. Sacrificial layer 906 fills up these grooves and stiction bump 1106 are created underneath sacrificial layer 906. FIG. 11H illustrates the protruding structures of stiction bump 1106 inside the cavity when sacrificial layer 906 is removed underneath insulating layer 118 and resistive conductor layer 104. FIGS. 11A-11H illustrate one method of forming stiction bumps. It should be appreciated that various other methods may be used to form stiction bumps in an insulating layer 118 of a MEMS heating device.

Figure 12:
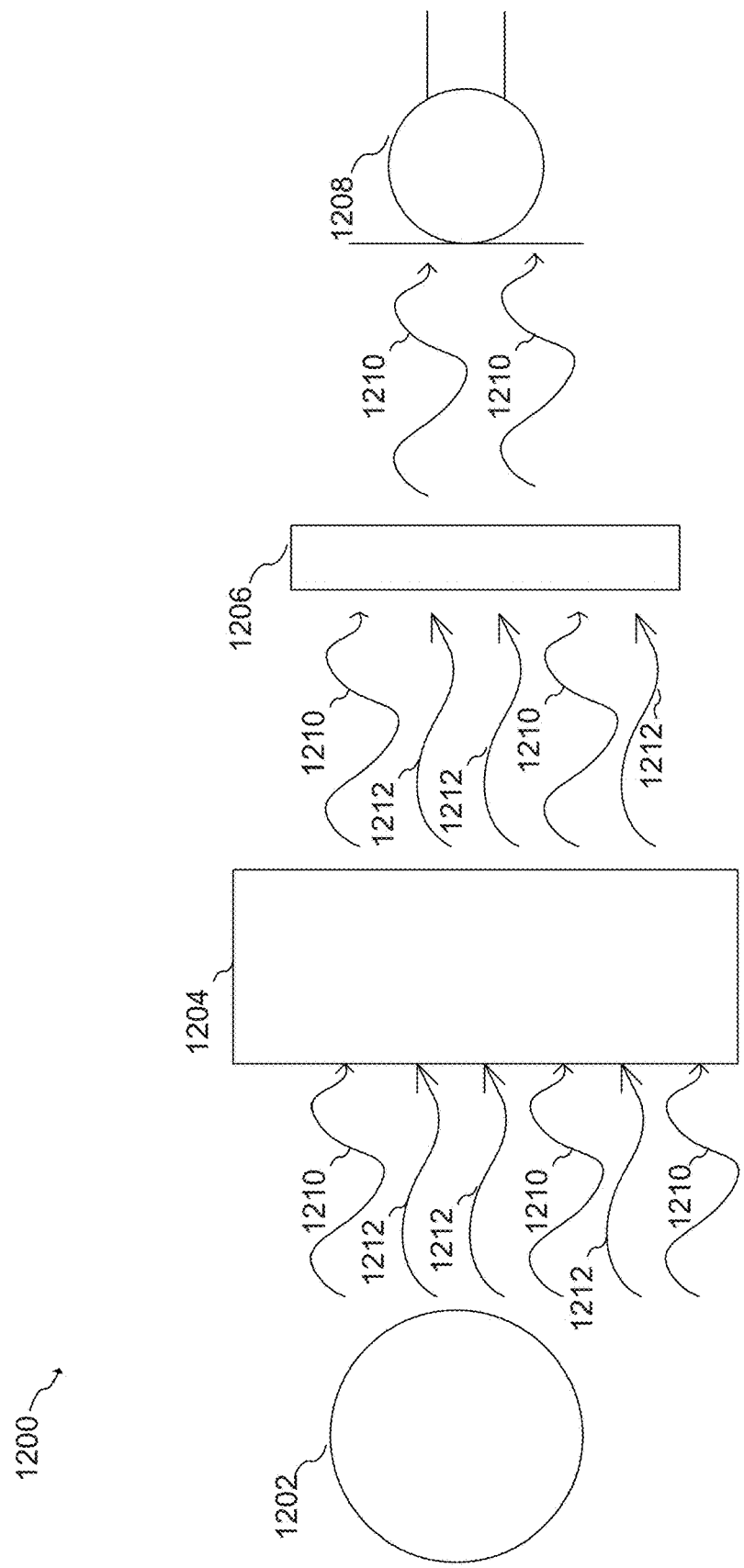
FIG. 12 illustrates an embodiment photoacoustic sensor (PAS) using an embodiment MEMS heating device.

The device described here can be used in a number of applications. In one example, a photoacoustic gas sensor (PAS) device includes an embodiment MEMS heating element used as an emitter of light source when heated to a specific temperature. FIG. 12 illustrates such an embodiment PAS device 1200 that includes an emitter module 1202, an optical path 1204, an infra-red (IR) filter 1206 and a detector or a pressure sensitive module 1208. Emitter 1202 may be formed by resistive conductor layer suspended above a cavity and a substrate. Optical path 1204 may be formed by a volume that may be filled with a gaseous media that is being analyzed. IR filter 1206 may be formed by different layers, for example, metal, monocrystalline silicon or poly silicon. In various embodiments, IR filter 1206 may be formed in the same substrate as emitter 1202 separated by a distance. Different types of detectors may be used as pressure sensitive module 1208, for example, a microphone to convert the acoustic waves to electric signals. In another embodiment, a photo-detector may be used where incoming light signals may be measured. In another embodiment, emitter module 1202 and pressure sensitive module 1208 may be implemented on different silicon substrate. In another embodiment, a loudspeaker may be designed by having audible signals generated by emitter module 1202 generated based on excitations.

FIG. 12 also illustrates excitations 1210 and 1212 generated by emitter module 1202 that represent different wavelengths. Excitations 1210 represent a specific wavelength that is excited by the gaseous media used to be analyzed. Excitations 1212 represent all other wavelengths except the wavelength of excitations 1210. Gaseous media in optical path 1204 absorbs and reduces energy for excitations 1210 as shown by the output excitations of optical path 1204. These excitations propagate as acoustic waves through IR filter 1206 that is filled with a reference gas.

IR filter 1206 acts as a band pass filter and allows the excitations 1210 to pass through. Excitations 1212 are filtered by IR filter 1206 and do not pass through IR filter 1206. The acoustic waves caused by the emitter pulses generated by the emitter module interacting with the gas to be analyzed propagate to detector or pressure sensitive module 1208. Pressure sensitive module 1208 is used to detect a pressure variation of the incoming waves. Information contained in the electric signals generated by pressure sensitive module 1208 is further used for determining composition of the gas. In an embodiment, pressure sensitive module 1208 may be implemented with a speaker.

Figure 13A:
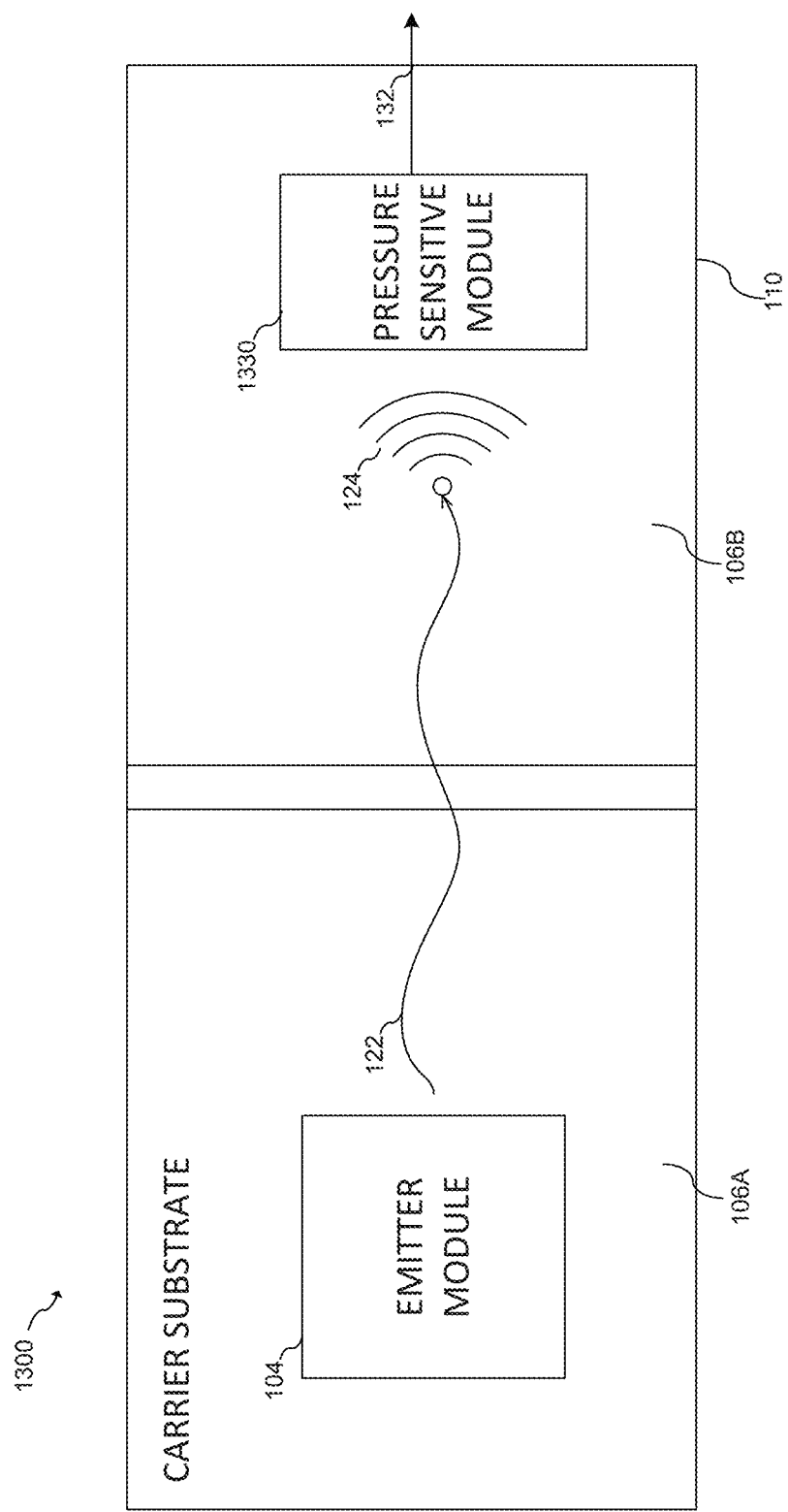
FIGS. 13A and 13B, collectively
Figure 13B:
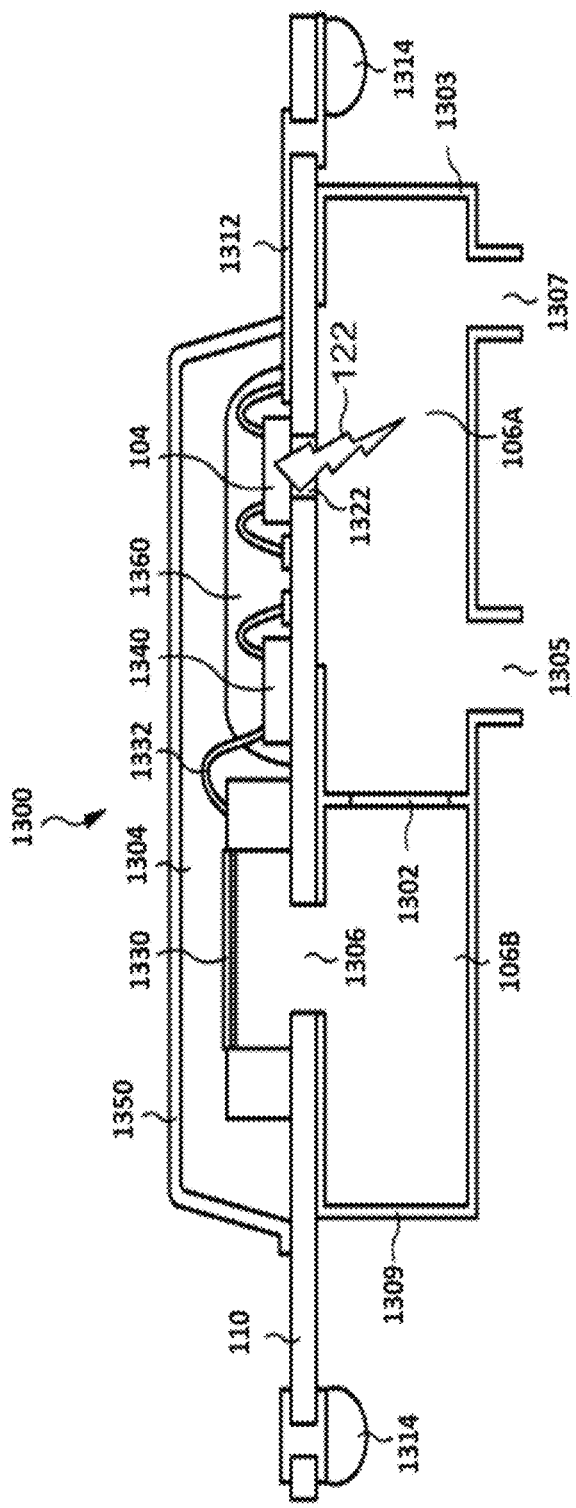
Figure 14:
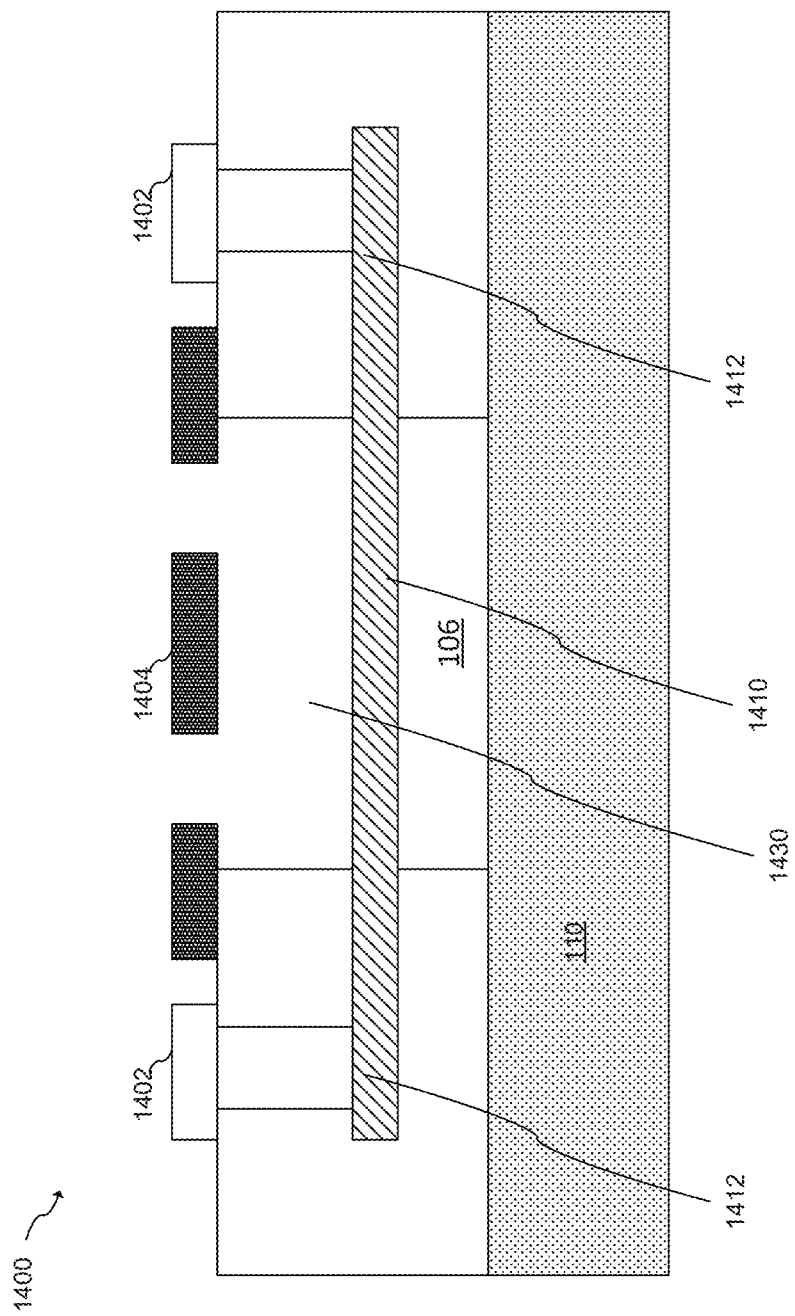
FIG. 14 illustrates another example of and implementation of embodiments of the present invention.

Two specific examples will now be described with respect to FIGS. 13 and 14. FIG. 13 is taken from FIG. 2 of co-pending application Ser. No. 14/052,959 (published as "Photoacoustic Gas Sensor Device and A Method for Analyzing Gas") and FIG. 14 is taken from FIG. 4 of co-pending application Ser. No. 14/052,962 (published as "Semiconductor Device for Emitting Frequency Adjusted Infrared Light") both of which are incorporated here by reference. The numbers in FIGS. 13A, 13B and 14 are left as published in their specifications and applications.

In the examples of FIGS. 13A and 13B, the emitter module (referred to as 120 in the above mentioned reference) can be implemented using a MEMS heating structure 104 described herein. In FIGS. 13A and 13B the emitter module is implemented by heating element 104 and thus referred as emitter module 104 in the description below. FIG. 13A illustrates a schematic illustration of a photoacoustic gas sensor device 1300 for analyzing gas according to an embodiment. The photoacoustic gas sensor device 1300 comprises an emitter module 104 and a pressure sensitive module 1330 arranged on a common substrate 110. The emitter module 104 is able to or configured to emit light pulses 122. The pressure sensitive module 1330 is arranged within a reference gas volume 106B. The reference gas volume 106B is separated from a volume 106A intended to be filled with a gas to be analyzed. The pressure sensitive module 1330 generates a sensor signal 132 indicating information on an acoustic wave 124 caused by light pulses 122 emitted by the emitter module 104 interacting with a reference gas within the reference gas volume 106B.

FIG. 13B illustrates a cross-section of a photoacoustic gas sensor device 1300 of according to an embodiment. Photoacoustic gas sensor device 1300 includes emitter module 104, pressure sensitive module 1330, and an analyzing module 1340 that are arranged on the same side of a common substrate 110. Emitter module 104 emits light pulses 122 through the hole or window 1322 into the volume 106A intended to be filled with the gas to be analyzed. The part of reference gas volume 106B located opposite to pressure sensitive module 1330 is enclosed by a housing 1309 neighboring the housing 1303 of volume 106A. Common substrate 110 comprises a hole 1306 between the pressure sensitive module 1330 and reference gas volume 106B. A lid or housing 1350 covers the pressure sensitive module 1330 and an analyzing module 1340. The analyzing module 1340 is laterally arranged between pressure sensitive module 1330 and emitter module 104. Emitter module 104 and analyzing module 1340 is optionally protected by a casting compound 1360. The reference gas volume 106B is enclosed by the housing 1303 comprising a gas outlet 1305 and a gas inlet 1307. The carrier substrate 110 may comprise one or more electrical contacts 1314. An electrical grounding contact 1312 may be used to contact shielding lid 1350 to common substrate 110.

In the example of FIG. 14, the lateral emitter structure 1410 can be implemented by an embodiment heating element 104 as described herein. FIG. 14 illustrates a schematic cross-section of a semiconductor device 1400 for emitting frequency-adjusted infrared light according to an embodiment. Visible light will also be emitted (Black/Gray body radiation according to Planck's law).

The semiconductor device 1400 comprises a semiconductor substrate 110 and a lateral emitter structure 1410 (e.g. IR-emitter element) arranged within a metal layer (e.g. copper, aluminum, tungsten, titan or titan nitride) or a semiconductor layer (e.g. monocrystalline silicon or poly silicon) separated from the semiconductor substrate 110 by a cavity 106. The lateral emitter structure 1410 comprises edge regions 1412 surrounding the part of lateral emitter structure 1410 mainly (more than 50% of the light intensity) contributing to the emitted infrared light laterally extending into insulating material (e.g. silicon dioxide) formed by insulating layers, for example. The lateral emitter structure 1410 is electrically connected at opposite sides with the edge region 1412 by electrical contacts 1402 (e.g. vias, filament contact) to be connected to an external current source or connected to an emitter control module on the same semiconductor die. The lateral filter structure 1404 (e.g. photonic crystal filter) is located above the lateral emitter structure 1410 by the lateral air gap 1430.

Figure 15:
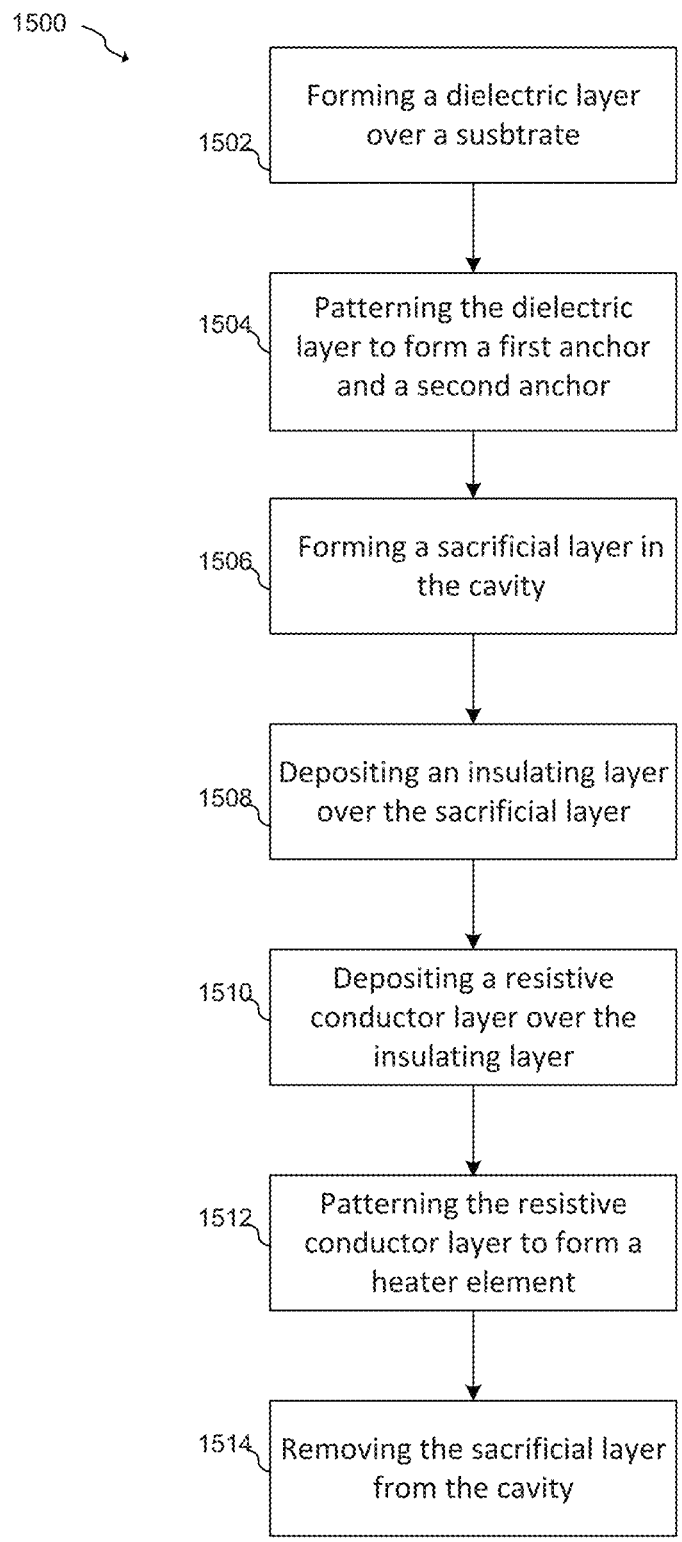
FIG. 15 illustrates a flow diagram of an embodiment method for forming a MEMS device.

FIG. 15 illustrates a flowchart of a method 1500 for manufacturing a MEMS heating device according to an embodiment. The method 1500 begins at step 1502 that includes forming a dielectric layer over a substrate. In step 1504, the dielectric layer is patterned to form a first anchor and a second anchor. The first and the second anchors are separated by a cavity above the substrate. In step 1506, a sacrificial layer is formed in the cavity so that actual mems device can be deposited. In step, 1508 an insulating layer is deposited over the sacrificial layer. In an embodiment, a thickness of the insulating layer is between 0.1 to 0.5 of a thickness of the layer of the heating element. In step 1510, a resistive conductor layer to form the heating element is deposited above the insulating layer. In step 1512, the resistive conductor layer is patterned to form the heating element. The heating element can be made of many different shapes, for example, in a shape of a rectangle or a serpentine. In step 1514, the sacrificial layer is removed underneath the insulating layer to form the actual cavity over which the heating element is suspended.

According to some embodiments described herein, advantages may include adding functionality to an integrated product. Some embodiments may include a heating element and control circuits integrated in a same semiconductor die. Such embodiments may advantageously include no extra masks or only a single extra mask during the fabrication sequence. Another advantage of some embodiments may include integrated temperature sensing functionality. Integration in a single semiconductor may also advantageously lead to improved performance and decreased cost in some embodiments. A further advantage of some embodiments may include providing heating for a subject that may be placed in contact with the heating element or a small distance apart in a single package. Such embodiments may advantageously improve heating performance, increase thermal efficiency, and the like As discussed above, the present invention includes a number of embodiments. It is noted that various aspects of the embodiments can be combined. In one embodiment, a method is used for operating a MEMS element that comprises a movable heater element overlying a substrate. The method comprises heating the movable heater element by causing a current to flow through the movable heater element while the movable heater element is spaced from the substrate; and cooling the movable heater element by causing the movable heater element to physically contact while being electrically isolated from the substrate.

Implementations may include one or more of the following features. Cooling the movable heater element can be accomplished by causing a voltage difference between the movable heater element and the substrate and discontinuing the current flow through the movable heater element. Cooling the movable heater element can be accomplished by generating an electro-static force between the substrate and the heater element by connecting the substrate to a different potential than the movable heater element. Cooling the movable heater element can be accomplished by generating an actuation force on the heater element by an expansion of a first piezo and a second piezo, where the first piezo is located on a first end of the heating element and a second piezo is located on a second end of the heating element. Heating the movable heater element can be accomplished by generating light by the movable heater element.

In another embodiment, a method is used for forming a micro electro-mechanical system (MEMS) heater element. The method comprises forming a dielectric layer over a substrate; patterning the dielectric layer to form a cavity within the dielectric layer; forming a sacrificial layer in the cavity; depositing an insulating layer over the sacrificial layer; depositing a resistive conductor layer over the insulating layer; patterning the resistive conductor layer to form a heater element that overlies the cavity and extends to two regions of the dielectric layer; and removing the sacrificial layer from the cavity so that a portion of the heater element is spaced from the substrate.

Implementations may include one or more of the following features. The method could also comprise forming a first contact at a first end of the resistive conductor layer and a second contact at a second end of the resistive conductor layer. The method could also comprise depositing a second insulating layer over the resistive conductor layer to encapsulate the heater element. A thickness of the second insulator layer can be between 0.1 and 0.5 of a thickness of the heater element. The insulator and the second insulator can comprise silicon nitride. The insulator and the second insulator can comprise a material with high tensile strength. The method could also comprise forming an array of stiction bumps at a surface of the insulator layer.

In another embodiment, a MEMS device comprises: a substrate; an electrically movable heating element having a first node and a second node, where the first node is coupled to a first terminal of a first voltage source and the second node is coupled to a reference voltage source; a first anchor anchoring the first node and a second anchor anchoring the second node of the electrically movable heating element to the substrate; and a cavity between the first and the second anchors and between the electrically movable heating element and the substrate.

Implementations may include one or more of the following features. The first voltage source can be configured to provide a first voltage to the first node of the electrically movable heating element. The electrically movable heating element can be configured to be cooled down by having the second node of the electrically movable heating element removed from the reference voltage source and creating an equipotential surface across the electrically movable heating element. The substrate can be connected to the reference voltage source so that an electrostatic force can be made between the electrically movable heating element and the substrate to actuate the electrically movable heating element to make contact to the substrate.

The electrically movable heating element can be encapsulated with silicon nitride. An array of electrically movable heating elements can be arranged above the substrate, where the electrically movable heating elements in the array can be controlled in a group. The electrically movable heating elements in the array can be controlled separately by an array of first voltage sources.

The MEMS device can further comprise a control circuit configured to provide a current through the movable heating element during a heating period and causing an infra-red light emission. The MEMS device can further comprise a spring support coupling the heating element to the first and second anchors. The MEMS device can further comprise a membrane, the heating element comprising a serpentine structure overlying the membrane, the spring structure being formed between the membrane and the first and second anchors.

In another embodiment, a MEMS device comprises a region of material with a cavity formed therein; an movable membrane anchored to the region of material and overlying the cavity, the movable membrane comprising an electrically movable heating element; a first piezo material physically attached the movable membrane at a first portion of the region of material; and a second piezo material physically attached the movable membrane at a second portion of the region of material. The first and second piezo materials are configured to cause the membrane to move between a first position at a top of the cavity to a second position within the cavity.

Implementations may include one or more of the following features. The heating element can comprise a serpentine structure overlying the membrane. The MEMS device can further comprise a heat spreader structure formed in the same layer as the heating element, the heat spreader structure being electrically insulated from the heating element.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for operating a MEMS element that includes a movable heater element overlying a substrate, the method comprising:
    heating the movable heater element by causing a current to flow through the movable heater element while the movable heater element is spaced from the substrate; and
    cooling the movable heater element by causing the movable heater element to physically contact the substrate while being electrically isolated from the substrate.

2. The method of claim 1, wherein cooling the movable heater element comprises causing a voltage difference between the movable heater element and the substrate and discontinuing the current flow through the movable heater element.

3. The method of claim 1, wherein cooling the movable heater element comprises generating an electro-static force between the substrate and the heater element by connecting the substrate to a different potential than the movable heater element.

4. The method of claim 1, wherein cooling the movable heater element comprises generating an actuation force on the heater element by an expansion of a first piezo and a second piezo, wherein the first piezo is located on a first end of the heater element and the second piezo is located on a second end of the heater element.

5. The method of claim 1, wherein heating the movable heater element comprises generating light by the movable heater element.

6. A MEMS device comprising:
    a substrate;
    an electrically movable heating element having a first node and a second node, wherein the first node is coupled to a first terminal of a first voltage source and the second node is coupled to a reference voltage source;
    a first anchor anchoring the first node and a second anchor anchoring the second node of the electrically movable heating element to the substrate; and
    a cavity between the first and the second anchors and between the electrically movable heating element and the substrate, wherein the first voltage source is configured to provide a first voltage to the first node of the electrically movable heating element.

7. The MEMS device of claim 6, wherein the electrically movable heating element is configured to be cooled down by having the second node of the electrically movable heating element removed from the reference voltage source and creating an equipotential surface across the electrically movable heating element.

8. The MEMS device of claim 6, wherein the substrate is connected to the reference voltage source so that an electrostatic force can be made between the electrically movable heating element and the substrate to actuate the electrically movable heating element to make contact to the substrate.

9. The MEMS device of claim 6, wherein the electrically movable heating element is encapsulated with silicon nitride.

10. The MEMS device of claim 6, wherein an array of electrically movable heating elements are arranged above the substrate, wherein the electrically movable heating elements in the array can be controlled in a group.

11. The MEMS device of claim 10, wherein the electrically movable heating elements in the array can be controlled separately by an array of first voltage sources.

12. The MEMS device of claim 6, further comprising a control circuit configured to provide a current through the movable heating element during a heating period and causing an infra-red light emission.

13. The MEMS device of claim 6, further comprising a spring support coupling the heating element to the first and second anchors.

14. The MEMS device of claim 13, further comprising a membrane, the heating element comprising a serpentine structure overlying the membrane, the spring support being formed between the membrane and the first and second anchors.

15. A MEMS device comprising:
   a region of material with a cavity formed therein;
   a movable membrane anchored to the region of material and overlying the cavity, the movable membrane including an electrically movable heating element;
   a first piezo material physically attached the movable membrane at a first portion of the region of material; and
   a second piezo material physically attached the movable membrane at a second portion of the region of material, wherein the first and second piezo materials are configured to cause the membrane to move between a first position at a top of the cavity to a second position within the cavity.

16. The MEMS device of claim 15, wherein the heating element comprising a serpentine structure overlying the membrane.

17. The MEMS device of claim 15, further comprising a heat spreader structure formed in the same layer as the heating element, the heat spreader structure being electrically insulated from the heating element.

* * * * *